United States Patent [19]

Ruoslahti et al.

[11] Patent Number: 5,206,347
[45] Date of Patent: Apr. 27, 1993

[54] ISOLATION AND USE OF RECEPTORS BINDING TO A PEPTIDE COLUMN

[75] Inventors: Erkki I. Ruoslahti, Rancho Santa Fe; Michael D. Pierschbacher, San Diego, both of Calif.

[73] Assignee: La Jolla Cancer Research Foundation, La Jolla, Calif.

[21] Appl. No.: 553,355

[22] Filed: Jul. 13, 1990

Related U.S. Application Data

[60] Continuation of Ser. No. 242,712, Sep. 9, 1988, abandoned, which is a division of Ser. No. 763,046, Aug. 6, 1985, abandoned.

[51] Int. Cl.$^5$ ................................................ C07K 3/18
[52] U.S. Cl. ...................................... 530/413; 530/395
[58] Field of Search ........................ 530/350, 395, 413

[56] References Cited

U.S. PATENT DOCUMENTS 4,988,621  1/1991  Ruoslahti et al. ............... 435/240.2

FOREIGN PATENT DOCUMENTS 8400540  2/1984  World Int. Prop. O.

OTHER PUBLICATIONS

Hansen et al. Biochem J. 201:629–633, 1982.
Cuatrecasas et al. Annu. Rev. Biochem. 40:259–278, 1971.
Alberts et al. *Molecular Biology of the Cell,* Garland Publishing Inc., New York, N.Y. 1983.
Weiss et al. J. Cell Biol. 88:630–636, 1981.
De Martelaere et al. Cell Biol. Intern. Reports 6(5):489–494, 1982.
Effects of a Serum Spreading Factor on Growth and Morphology of Cells in Serum-Free Medium, David Barnes et al., J. of Supramolecular Structure 14:47–63 (1980).
Cell Attachment on Replicas of SDS Polyacrylamide Gels Reveals Two Adhesive Plasma Proteins, Edward G. Hayman et al., J. of Cell Biology, vol. 95 95 (1982).
Identification and Isolation of a 140 kd Cell Surface Glycoprotein with Properties Expected of a Fibronectin Receptor, R. Pytela et al, Cell, vol. 40 191–198 Jan. 1985.
Dualistic Nature of Adhesive Protein Function; Fibronectin and Its Biologically Active Peptide Fragments Can Autoinhibit Fibronectin Function, K. Yamada et al., J. of Cell Biology vol. 99 Jul. 1984.
Reversible Cross-linking of Cellular Components of Adherent Fibroblasts to Fibronectin and Lectin-Coated Substrata, J. D. Alpin et al. 1981.
Fibronectin and Proteoglycans as Determinants of Cell-Substratum Adhesion, Lloyd A. Culp, et al., J. of Supramolecular Structure 11:401–427 (1979).
Isolation and Purification of Collagen al(1) Receptor from Human Platelet Membrane, Thomas M. Chiang et al., J. of Biological Chemistry vol. 257 (1982).
Monoclonal Antibodies Which Alter the Morphology of Cultured Chick Myogenic Cells, Jeffrey M. Greve et al., J. of Cellular Biochemistry 18:221–229 (1982).
Relationships Between Fibronectin and the Cytoskeleton, Richard O. Hynes (1981) pp. 100–137.
Direction Association of Fibronectin and Actin Molecules in Vitro, Jorma Keski-Oja et al. J. of Cell Biology vol. 85 1980 pp. 527–533.

(List continued on next page.)

*Primary Examiner*—Robert A. Wax
*Assistant Examiner*—Keith C. Furman
*Attorney, Agent, or Firm*—Pretty, Schroeder, Brueggemann & Clark

[57] ABSTRACT

A method of isolating cell surface receptors utilizing a short peptide sequence bound to an affinity column. Cell surface receptors which bind selectively to the short peptide and which are specific to various adhesion proteins may be isolated therewith from various cell preparations. These receptors, whose functional integrity has been maintained by the presence of the peptide ligand, are incorporated into liposomes and used to deliver specific compounds inside the liposomes to select tissues containing the specific adhesion proteins.

9 Claims, No Drawings

OTHER PUBLICATIONS

Isolation of a Collagen-Dependent Cell Attachment Factor, Nature vol. 250 Jul. 1974.

Ganglioside Inhibition of Fibronectin-Mediated Cell Adhesion to Collagen, Hynda Kleinman et al., Proc. Natl. Acad. Set vol. 76, 1976.

Cell Surface Heparan Sulfate Mediates Some Adhesive Responses to Glycosaminoglycan-Binding Matrices, Including Fibronectin, John Laterra et al., J. of Cell Biology vol. 96, 1983.

Thiol-Sensitive Sites in Cell Adhesion, Douglas McAbee et al. Biochem. Journal 1982, 473-478.

A Monoclonal Antibody Detaches Embryonic Skeletal Muscle from Extracellular Matrices, N. T. Neff, et al., J. of Cell Biology vol. 95, Nov. 1982.

Calcium Ions Protect Cell-Substratum Adhesion Receptors Against Proteolysis, N. Oppenheimer-Marks et al., Experimental Cell Research 152 (1984) 467-475.

Plasma Membrane Glycoprotein Which Mediates Adhesion of Fibroblasts to Collagen, Pearlstein, Nature vol. 262, 1976.

Cross-Linking of Fibronectin to Sulfated Proteoglycans at the Cell Surface, Margaret Perkins, et al. Cell, vol. 16, 941-952, 1979.

Interactions Among Heparin, Cold-Insoluble Globulin, and Fibrinogen in Formation of the Heparin-Precipitable Fraction of Plasma, Nicholas E. Statharis, et al., J. of Clinical Investigation vol. 60, 1977.

Cell Surface Molecules and Fibronectin-Mediated Cell Adhesion: Effect of Proteolytic Digestion of Membrane Proteins, Guido Tarone et al., J. of Cell Biology vol. 94, 1982.

Laminin-A Blycoprotein from Basement Membrane, Rupert Timpl et al, J. of Biological Chemistry, vol. 254 (1979).

Isolation of a Cell Surface Receptor Protein for Laminin from Murine Fibrosarcoma Cells, Herbert Malinoff et al., J. of Cell Biology vol. 96, 1983.

Isolation of a Laminin-Binding Protein from Muscle Cell Membranes, Herve Lesot, et al., The EMBO Journal vol. 2, No. 6, 1983.

Isolation and Characterization of a Collagen-Binding Glycoprotein from Chondrocyte Membranes, Jurgen Mollenhauer et al., The EMBO Journal vol. 2, No. 1, 1983.

Role of Collagenous Matrices in the Adhesion and Growth of Cells, Hynda Kleinman et al., J. of Cell Biology vol. 88, 1981.

Synthetic Peptide with Cell Attachment Activity of Fibronectin, Michael Pierschbacher et al., Proc. Natl. Acad. vol. 80, 1983.

Laminin from Rat Yolk Sac Tumor: Isolation, Particle Characterization and Comparison with Mouse Laminin, Eva Engvall et al, Archives of Biochemistry and Biophysics vol. 222, 1983.

Binding of Soluble Form of Fibroblast Surface Protein, Fibronectin, to Collagen, Eva Engvall et al., Int. J. Cancer 20, 1-5, 1977.

Concomitant Loss of Cell Surface Fibronectin and Laminin from Transformed Rat Kidney Cells, Edward Hayman et al, J. of Cell Biology vol. 88, 1981.

Serum Spreading Factor (Vitronectin) is Present at the Cell Surface and in Tissues, Edward Hayman et al., Proc. Natl. Acad. Sci. vol. 80, 1983.

Cell Attachment Activity of Fibronectin Can Be Duplicated by Small Synthetic Fragments of the Molecule, M. D. Pierschbacher et al. Nature, vol. 309, 1984.

Variants of the Cell Recognition Site of Fibronectin that Retain Attachment-Promoting Activity, M. D. Pierschbacher et al. Proc. Natl. Acad. Sci. vol. 81, 1984.

Location of the Cell Attachment Site in Fibronectin with Monoclonal Antibodies and Proteolytic Fragments of the Molecule, M. D. Pierschbacher et al., Cell, vol. 26, 1981.

The Cell Attachment Domain of Fibronectin, M. D. Pierschbacher et al. J. of Biological Chemistry, vol. 257, 1982.

Alignment of Biologically Active Domains in the Fibronectin Molecule, Erkki Ruoslahti et al., J. of Biological Chemistry, vol. 256, 1981.

Interaction of Soluble Fibroblast Surface Antigen with Fibrinogen and Fibrin, Erkki Ruoslahti et al., J. of Experimental Medicine vol. 141, 1975.

Fibronectin: Current Concepts of Its Structure and Functions, Erkki Ruoslahti et al., Coll. Res. vol. 1, 1981.

Localization of the Gangliosides GD2 and GD3 in Adhesion Plaques and on the Surface of Human Melanoma Cells, D. A. Cheresh et al. Proc. Natl. Acad. Sci. vol. 81, 1984.

Inhibition of Human Melanoma Cell Growth in Vitro by Monoclonal Anti-GD3-Ganglioside Antibody, W. G. Dippold et al. Cancer Research 44, Feb. 1984.

Chemical Characterization of a Neural Cell Adhesion Molecule Purified from Embryonic Brain Membranes, S. Hoffman et al., J. of Biological Chemistry, vol. 257, 1982.

Antisera Inhibiting Mammalian Cell Spreading and Possible Cell Surface Antigens Involved, P. Hsieh et al., J. of Cell Biology, 1980.

Membrane Glycoproteins Involved in Cell–Substratum Adhesion, K. A. Knudsen et al., Proc. Natl. Acad. Sci. vol. 78, 1981.

Antibody Affinity May Influence Antigenic Modulation of the Common Acute Lymphoblastic Leukemia Antigen in Vitro, T. W. Lebien et al. J. of Immunology, 1982.

Binding of Plasma Fibronectin to Cell Layers of Human Fibroblasts, P. J. McKeown–Longo et al., J. of Cell Biology, 1983.

New Surface Component of Fibroblast's Focal Contacts Identified by a Monoclonal Antibody, B. Gresch et al., Cell, vol. 31, 1982.

Inhibition of Fibronectin Receptor Function by Antibodies Against Baby Hamster Kidney Cell Wheat Germ Agglutinin Receptors, N. Oppenheimer et al., J. of Cell Biology vol. 95, 1982.

Studies of Cell Adhesion and Recognition I. Extent and Specificity of Cell Adhesion Triggered by Carbohydrate–Reactive Proteins (Clycosidases and Lectins) and by Fibronectin, H. Rauvala, J. of Cell Biology vol. 88, Jan. 1981.

Teratocarcinoma Cell Adhesion: Identification of a Cell–Surface Protein Involved in Calcium–Dependent Cell Aggregation, C. Yoshido et al., Cell, vol. 28, 1982.

Formation of Stress Fibres and Focal Adhesion Sites in Monensin–Exposed Cultured Human Fibroblasts in Response to Exogenously Added Cellular Fibronectin, V. P. Lehto et al., 1985.

Platelet Membrane Glycoprotein IIb–IIa: Member of a Family of Arg–Gly–Asp–Specific Adhesion Receptors, R. Pytela, et al.

Complete Amino Acid Sequence of Human Vitronectin Deduced from cDNA. Similarity of Cell Attachment Sites in Vitronectin and Fibronectin, S. Suzuki et al., The EMBO Journal vol. 4, 1985.

Detachment of Cells from Culture Substrate by Soluble Fibronectin Peptides, E. G. Hayman et al. J. of Cell Biology, 1985.

A 125/115 kDa Cell Surface Receptor Specific for Vitronectin Interacts with the Arginine–Glycine–Aspartic Acid Adhesion Sequence Derived from Fibronectin, R. Pytela et al., Proc. Natl. Acad. Sci. vol. 82, 1985.

Adhesion of Platelets to Laminin in the Absence of Activation, C. R. Ill, et al., J. of Cell Biology vol. 99, 1984.

Inhibition of Fibronectin Binding to Platelets by Proteolytic Fragments and Synthetic Peptides which Support Fibroblast Adhesion, M. Ginsberg et al. J. of Biological Chemistry, 1985.

The Effect of Arg–Gly–Asp–Containing Peptides on Fibrinogen and von Willebrand Factor Binding to Platelets, E. Plow, et al. Proc. Natl. Acad. Sci. vol. 82, 1985.

Cloning and Characterization of Two cDNAs Coding for Human von Willebrand Factor, J. Evan Sadler et al, Proc. Natl. Acad. Sci. vol. 82, 1985.

Effects of Fibronectin–Related Peptides on Cell Spreading, J. Siinut et al., In Vitro Cellular & Developmental Biology vol. 21, 1985.

The Amino Acid Sequence of the cx–Chain of Human Fibrinogen, R. F. Doolittle et al., Nature, vol. 280, 1979.

Analysis of Platelet Adhesion with a Radioactive Chemical Cross–Linking Reagent: Interaction of Thrombospondin with Fibronectin and Collagen, J. Lahav et al., Cell vol. 31, 1982.

Platelet Membrane Defects in Glanzmann's Thrombasthenia, D. R. Phillips et al., J. of Clinical Investigation vol. 60, 1977.

Inhibition of von Willebrand Factor–Platelet Interaction by Fibrinogen, G. Pietu, et al., Nature vol. 308, 1984.

Evidence that Three Adhesive Proteins Interact with a Common Recognition Site on Activated Platelets, E. Plow et al., J. of Biological Chemistry vol. 259, 1984.

Platelets Have More Than One Binding Site for von Willebrand Factor, Z. Ruggeri et al. J. Clin. Investigation vol. 72, 1983.

Glanzmann Thrombasthenia: Deficient Binding of von Willebrand Factor to Thrombin–Stimulated Platelets, Z. Ruggeri et al., Proc. Natl. Acad. Sci. vol. 79, 1982.

Platelet–Collagen Adhesion: Inhibition by a Monoclonal Antibody that Binds Glycoprotein IIB, P. J. Shadle et al., J. of Cell Biology vol. 99, 1984.

Identification of Two Structurally and Functionally Distinct Sites on Human Platelet Membrane Glycoprotein IIb–IIa Using Monoclonal Antibodies, R. P. McEver, J. of Biological Chemistry vol. 258, 1983.

Purification of Glycoproteins IIb and III from Human Platelet Plasma Membranes and Characterization of a Calcium–Dependent Glycoprotein IIb–III Complex, L. K. Jennings et al., J. of Biological Chemistry vol. 257, 1982.

Detachment of Cells from Culture Substrate by Soluble Fibronectin Peptides, E. G. Hayman et al., J. of Cell Biology vol. 100, 1985.

Interaction of Ap-2, A Monoclonal Antibody Specific for the Human Platelet Glycoprotein IIb–IIa Complex with Intact Platelets, D. Pidard et al., J. of Biological Chemistry vol. 258, 1983.

ADP-Sependent Common Receptor Mechanism for Binding of von Willebrand Factor and Fibrinogen to Human Platelets, J. Timmons, et al. Proc. Natl. Acad. Sci. vol. 81, 1984.

The Area-Code Hypothesis: The Immune System Provides Clues to Understanding the Genetic and Molecular Basis of Cell Recognition During Development, L. Hood, et al, J. of Supramolecular Structure 7:531–559, 1977.

Secreted Alpha Granule Proteins, D. F. Mosher et al., 1985.

Interaction of Purified Type IIb von Willebrand Factor with the Platelet Membrane Glycoprotein Ib Induces Fibrinogen Binding to the Glycoprotein IIb/IIIa Complex and Initiates Aggregation, L. DeMarco, Proc. Natl. Acad. Sci. vol. 82, 1985.

Loss of Fibrinogen Receptors from the Platelet Surface During Simulated Extracorporeal Circulation, J. Musial et al, J. of Laboratory and Clinical Medicine vol. 105, 1985.

A Murine Monoclonal Antibody that Completely Blocks the Binding of Fibrinogen to Platelets Produces a Thrombasthenic-like State in Normal Platelets and Binds to Glycoproteins IIb and/or IIIa, B. S. Coller, et al, J. Clin. Invest. vol. 72 (1983).

Reconstitution of the Purified Platelet Fibrinogen Receptor, L. V. Parise et al., J. of Biological Chemistry, 1985.

Inhibition of Fibrinogen Binding to Stimulated Human Platelets by a Monoclonal Antibody, J. S. Bennett et al., Proc. Natl. Acad. of Sci. vol. 80, 1983.

ISOLATION AND USE OF RECEPTORS BINDING TO A PEPTIDE COLUMN

This application is a continuation of application Ser. No. 242,712, filed Sep. 9, 1988, now abandoned, which is a divisional of application Ser. No. 763,046, filed Aug. 6, 1985, now abandoned.

BACKGROUND OF THE INVENTION

This invention relates generally to the field of cell biology and more specifically to cell adhesion systems.

Multicellular organisms, such as man, have some $10^{14}$ cells which may be divided into a minimum of fifty types, such as blood cells and nerve cells, etc. During the course of growth and development, cells adhere to other cells, or to extra-cellular materials, in specific and orderly ways. Such cell adhesion appears to be of importance in mediating patterns of cellular growth, migration and differentiation, whereby cells develop specialized characteristics, so as to function as, for example, muscle cells or liver cells. Cell adhesion mechanisms also appear to be implicated in dedifferentiation, notably where cells lose their specialized forms and become metastasizing cancer cells.

The adhesion of cells to other cells or extracellular substrates appears to be at least a two step process: a cell must first recognize an appropriate site for attachment and thence selectively attach to it. Certain molecules have been identified which promote the attachment of cells to a solid substrate. Among these are fibronectin and vitronectin, two glycoproteins which are found in human plasma and serum. Unequal concentrations of specific adhesion promoting proteins are present in various tissues, indicating that their functions may be somewhat different.

Adhesive proteins can be used, for example, to coat the surfaces of containers used for growing cells in tissue culture so as to promote the attachment of such cells. Conversely, by suspending such molecules in the culture medium, the cells may be discouraged from attaching to the substrate. Because various types of cells will only grow effectively when attached to a solid substrate, the regulation of attachment is important in enabling the culturing of cells.

To gain further insight into the mechanisms of cell adhesion so as to permit manipulation and control, an understanding of the recognition sites on the cells themselves is necessary. Recently, a cell surface receptor specific to fibronectin has been isolated and described (Pytela, et al., Cell 40:191, (1985)). This fibronectin receptor appears to specifically recognize and bind a portion of the fibronectin molecule which is composed of the amino acid sequence arginine-glycine-aspartic acid (Arg-Gly-Asp). Upon introducing fibronectin receptors to a solid substrate to which is attached fibronectin, the receptors will selectively bind the protein and can thus be manipulated.

Because of the critical role of cell surface receptors in regulating cell growth and differentiation both in vivo and in vitro, there exists a need for the isolation and purification of additional cell surface receptors. Specifically, there is a need for cell surface receptors which may be specific to certain cell types, or exist in greater porportion in certain cell types, than the previously recognized fibronectin receptors. Further there exists a need to identify cell surface receptors which can be selectively manipulated with small and easily obtained molecules. Moreover, there exists a need for a method to protect the functional integrity of cell surface receptors during such manipulations. The present invention satisfies these needs and provides additional advantages as well.

SUMMARY OF THE INVENTION

The present invention provides a novel method of isolating cell surface receptors utilizing a short peptide sequence bound to an affinity column. Cell surface receptors which bind selectively to the peptide and which are specific to various adhesion proteins are isolated from various cell preparations. Cell surface receptors may be incorporated into the surface membranes of liposomes thereby targeting the liposomes to certain tissues. Moreover, such liposomes incorporating the cell surface receptors may be used to deliver specific compounds contained inside the liposomes selectively to tissues exhibiting the specific adhesion proteins.

One aspect of the present invention is the isolation from osteosarcoma or other mesenchymal cells of a receptor molecule which specifically interacts with vitronectin. The receptor is composed of at least two polypeptides having apparent molecular weights of 115 and 125 kilo Daltons (kD) as determined by SDS-PAGE under reducing conditions. The polypeptides are accessible to lactoperoxidase-catalyzed iodination at the cell surface. When incorporated into the membranes of liposomes, these polypeptides mediate the specific binding of the liposomes to vitronectin, but not to fibronectin. Moreover, antibodies raised against the vitronectin receptor do not detectably react with another cell surface receptor, the fibronectin receptor.

Another aspect of the invention is the isolation from platelet cells of a receptor which recognizes not only the extracellular matrices fibronectin and vitronectin, but the blood clot factor fibrinogen, and apparently von Willebrand factor as well. Thus, this cell surface receptor has elements of a universal receptor binding to tissue components, including both extracellular matrices and blood clot factors.

In another aspect of the present invention, the cell surface receptors are incorporated into the membranes of liposomes by subjecting a detergent solution containing the receptor polypeptides and a phospholipid to dialysis against a detergent-free buffer. Such liposomes are then used to target the contents of the liposomes to tissues containing various molecules. The vitronectin receptor liposomes are useful in targeting liposomes in tissues rich in connective tissue. For instance, fibrosis of various organs may be treated with liposomes loaded with connective tissue-degrading enzymes using receptor-mediated targeting. Moreover, because many tumors contain large amounts of connective tissue, drugs may be delivered to tumors with some degree of selectivity using receptor liposomes. The platelet receptor may be useful in targeting liposomes to intravascular blood clots such as those causing myocardial infarction as blood clots contain fibrin and fibronectin, both of which can serve as ligands for the platelet receptor, and liposomes containing this receptor at their surface can be expected to bind specifically to blood clots. Agents designed to dissolve the clot could thus be delivered specifically to the clot itself. Liposomes containing platelet receptor or one of the other receptors may also be used to compete with the adhesion of platelets to fibrin clots or vascular walls in which the extracellular matrix has become exposed as a result of loss of the endothelial cell lining.

In another aspect of the invention, the cell surface receptors are protected by the continuous presence of their respective ligands, such as a peptide. Such protection results in the maintenance of the functional integrity of the cell receptor itself, thereby permitting use of the receptor, for example, in liposomes.

Other features and advantages of the present invention will become apparent from the following detailed description which illustrates, by way of example, the principles of the invention.

DETAILED DESCRIPTION OF THE PREFERRED EMBODIMENT

The present invention involves a novel method of isolating cell surface receptors, certain isolated cell surface receptors, the protection of their functional integrity, their incorporation into liposomes and the use thereof to target therapeutic agents to specific tissues.

Cell surface receptors are isolated by utilizing an affinity column to which is bound a short peptide sequence. Receptors which bind to the peptide and which are specific to various adhesion proteins are isolated from various tissue preparations, such as mesenchymal cells and platelets. These receptors may be incorporated into the surface membranes of liposomes so as to target the liposomes to certain tissue components, such as extracellular matrix and certain cells, thereby providing a mechanism for delivering the contents of the liposomes to tissues exhibiting the specific adhesion proteins.

Certain cell surface receptors are isolated through the use of a column packed with SEPHAROSE beaded agarose matrix to which is attached a short peptide. This peptide contains the amino acid sequence Arg-Gly-Asp, which is the binding site of fibronectin. By applying cell extract preparations of different cells to the column, cell surface receptors contained in the preparations are bound to the column. The receptors are then selectively eluted by flushing the column with a solution containing the peptide. The presence of the ligand protects the receptor, thereby maintaining its functionality.

One cell surface receptor so isolated is specific to vitronectin, and can be isolated from mesenchymal cells, such as osteosarcoma cells. Vitronectin, also called serum spreading factor, is a glycoprotein derived from human serum and plasma which can effect adhesion between certain cells and substrates. The active component of vitronectin is a protein composed of two closely related polypeptides having masses of 65 and 75 kD, respectively. Insoluble vitronectin is found in human connective tissue. The receptor comprises at least two polypeptides having masses of 115 and 125 kD.

Platelets are a class of cell-like structures found in the blood which exhibit complex adhesive interactions, notably aggregation of platelets and adhesion to extra cellular substrata. The cell surface receptor isolated from platelet preparations by means of the SEPHAROSE beaded agarose matrix-peptide column binds not only to fibronectin, but to vitronectin, fibrinogen and apparently von Willebrand factor as well. This receptor, therefore, appears to be a very generalized receptor.

Cell surface receptors can be incorporated into liposomes. In such a combination the receptors confer a specificity to the liposomes which permits them to deliver therapeutic agents to targeted tissues. A unique feature of the receptor liposomes is that rather than binding to cells, which targeted liposomes are usually designed to do, they will have affinity to extracellular matrices or fibrin and fibronectin in blood clots. When coated onto the surface of prosthetic materials, the receptors would facilitate the bonding of a prosthesis, such as artificial skin, with extracellular matrix.

EXAMPLE I

SEPHAROSE Beaded Agarose Matrix-Peptide Column

A synthetic peptide having the amino acid sequence Gly-Arg-Gly-Asp-Ser-Pro (GRGDSP) (prepared to specification by Peninsula Laboratories, San Carlos, Calif.) is coupled to a cyanogen bromide activated agarose affinity matrix such as SEPHAROSE beaded agarose matrix by the method of Axen, et al., Nature 214:1302 (1967).

EXAMPLE II

Isolation of the Vitronectin Receptor

MG-63 osteosarcoma cells were grown on 175 cm$^2$ tissue culture dishes in Dulbecco's modified Eagle's medium (DMEM) supplemented with 5% fetal calf serum, glutamine and penicillin/streptomycin. For subculturing and harvesting, confluent layers of cells were incubated in 1 mM ethylene diamintetraacetic acid (EDTA) for 15 minutes. For surface iodination, cells were harvested from confluent cultures, collected by centrifugation and resuspended in phosphate buffered saline (150 mM NaCl, 10 mM sodium phosphate, 1 mM CaCl$_2$, 1 mM MgCl$_2$, pH 7.3) containing 0.2 mM PMSF. The suspended cells were radioiodinated with Na$^{125}$I according to Lebien et al., J. Immunol. 129:2287 1982), which is incorporated by reference, and lysed in 200 mM octyl-$\beta$-D-glucopyranoside (octylglucoside, Behring Diagnostics, La Jolla, Calif.).

An octylglucoside extract containing 10$^8$ cells in 1 ml was applied to the affinity matrix which was then eluted with buffer containing detergent and the synthetic peptide, Gly-Arg-Gly-Asp-Ser-Pro (GRGDSP) which is a cell attachment-promoting peptide including the fibronectin attachment sequence. The elution was carried out by slowly washing the column with 1 volume of column buffer supplemented with 1 mg/ml (1.5 mM) of GRGDSP over a period of one hour. The elution released two polypeptides from the column having apparent molecular weights of 115 and 125 kD as determined by SDS-PAGE under reducing conditions as described in Laemmli, Nature 227:680 (1970). Samples were boiled for 3 minutes in the presence of 3% SDS, with or without 5% 2-mercaptoethanol, and electrophoresed on 7.5% acrylamide gels. The molecular weight markers used were myosin (200 kD), $\beta$-galactosidase (116 kD), phosphorylase B (94 kD) and ovalbumin (43 kD). Gels were silver-stained using a reagent kit (BioRad, Richmond, Calif.), according to manufacturer's instructions. Autoradiography was performed using KODAK XAR autoradiography film X-Ray film placed between the dried gel and a Cronex Lightning Plus intensifying screen (DuPont, Newton, Conn.) and was continued for 1 to 3 days at −70° C.

EXAMPLE III

Alternative Isolation of the Vitronectin Receptor

Larger quantities of the receptor in an electrophoretically homogeneous form were obtained from human placenta. Two hundred grams of fresh-frozen human placental tissue were extracted with 200 ml octylglucoside or octylthioglucoside solution. The resulting extract was applied on a 10 ml peptide-SEPHAROSE beaded agarose matrix column prepared and used as described above. The partially purified receptor obtained from the peptide column was further fractionated on a column of 1 ml wheat germ agglutinin-SEPHAROSE beaded agarose matrix (Pharmacia Fine Chemicals, Piscataway, N.J.), equilibrated with column buffer containing 0.1% NP-40 in the phosphate buffer saline detailed above. The receptor was eluted with 200 mM N-acetyl-glucosamine in the column buffer. The column fractions were analyzed by SDS-PAGE as described above, but the gel was stained with Coomassie blue.

EXAMPLE IV

Isolation of Platelet Receptor

Outdated human platelets (5 units) were harvested by centrifugation at 2200 rpm. The pellet was resuspended in Tyrode's buffer containing 1 mM $CaCl_2$, and platelets were again collected by centrifugation. Five ml of cold 10 mM phosphate, 150 mM $NaCl_2$, 1 mM $MgCl_2$, pH 7.3 (PBS), containing 50 mM octylthioglucoside (Behring Diagnostics, La Jolla, Calif.) and 3 mM PMSF were added to this pellet (5 ml). After resuspension of the pellet and incubation at 4° C. for 15 min., the lysate was centrifuged at 30,000 xg for 20 min. (4° C.) and the supernatant (5 ml) was applied to a GRGDSP-SEPHAROSE beaded agarose matrix column bed volume 10 ml). The affinity matrix had been prepared by incubating 120 mg of GRGDSP(K)-peptide (the lysine residue (K) was added to optimize coupling) with 10 ml of CNBr-SEPHAROSE beaded agarose matrix following the manufacturer's instructions. The extract was incubated with the affinity matrix overnight at 4° C., and the column was washed with 50 ml of PBS containing 25 mM octylthioglucoside and 1 mM PMSF. Elution of specifically bound components was accomplished by washing the column with 10 ml of column buffer containing 1 mg/ml of GRGDSP-peptide, and then with another 10 ml of column buffer. Finally, the column was washed with 8 M urea, 50 mM tris-HCl, pH 7.5, to release non-specifically bound proteins. Fractions (2.5 ml) were collected after the peptide solution was applied. Sixty $\mu$l-aliquots of each fraction were mixed with 20 $\mu$l of 12% SDS, 20% 2-mercaptoethanol, 60 mM TrisHCl, pH 6.8, boiled for 3 min., and electrophoresed on a 7.5% polyacrylamide gel according to the method of Laemmli, above. Protein bands were visualized by staining with Coomassie blue. The amount of protein recovered from the column was about 0.5 mg, as estimated by densitometric scanning of the gel bands.

EXAMPLE V

Incorporation of Vitronectin Receptor Into Liposomes

Phosphatidylcholine liposomes incorporating the cell surface receptors were prepared essentially by the method of Mimms et al., Biochemistry 20:883 (1981), which is incorporated by reference. Egg yolk phosphatidylcholine (Sigma, St. Louis, Mo.), $^3$H-phosphatidycholine (New England Nuclear, Boston, Mass.) and the appropriate radioiodinated cell surface receptor fractions were dissolved in column buffer. This solution was then dialyzed against a detergent-free buffer, PBS for 24 hours at 4° C., resulting in the formation of liposomes with an average diameter of approximately 200 nm, as judged by electron microscopy. In the case of the 115 and 125 kD polypeptides of the vitronectin receptor, about 90% of the protein radioactivity was found associated with the liposome fraction after the liposomes had been floated to the surface of a sucrose gradient by ultracentrifugation.

EXAMPLE VI

Binding of Vitronectin Receptor-liposomes to Vitronectin and Peptide Substrates Lipsomes incorporating the radioiodine labelled vitronectin receptor polypeptides were used to study the recognition specificity of the receptor. Polystyrene Microtiter plate wells (Linbro/Titertek, Inglewood, Calif.) were coated with extracellular matrix proteins and peptides including vitronectin, fibronectin, laminin and the synthetic peptides Gly-Arg-Gly-Asp-Ser-Pro (GRGDSP) and Gly-Arg-Gly-Glu-Ser-Pro (GRGESP). The vitronectin receptor-liposome preparation showed dose dependent binding to microtiter wells coated with vitronectin, but not fibronectin or laminin. Moreover, it bound to the GRGDSP peptide which contains the Arg-Gly-Asp sequence, but not the GRGESP peptide, which does not. The Arg-Gly-Asp sequence is therefore implicated in the binding of the liposomes containing the vitronectin receptor.

EXAMPLE VII

Use of the Receptor-liposome Preparation to Target Therapeutic Agents

Receptor liposomes are prepared as described above and a desired therapeutic agent is incorporated into them according to published methods (Hashimoto et al., Cancer Research 43:5328 (1983); Gregoriadis and Senior, Biochem. Soc. Trans. 12:337 (1984)) which are incorporated by reference. These conjugated liposomes are injected intravenously using 1–300 $\mu$mol of lipid per kg of body weight or applied locally. Such vitronectin receptor liposomes are used, for example, to target tissue degrading enzymes to tumors, which contain large amounts of connective tissue. Moreover, platelet receptor conjugated liposomes are used, for example, to deliver clot dissolving agents specifically to blood clots in the body, such as those causing a myocardial infarction.

EXAMPLE VIII

Use of the Receptor as a Coating on a Substrate

To coat a nonlipid surface with receptors, a receptor from a solution is covalently coupled to a surface such as plastic using one of the many well known methods available for such coupling. Receptor fragments that retain the ligand-binding activity but lack the membrane embedded portion of the molecule are advantageously used as they are more soluble than the complete receptor. Such materials coated with receptors are useful as prostheses where attachment of extracellular matrix is desired, such as, for example, artificial skin.

We claim:

1. A method for isolating cell surface receptors from a cell extract preparation, comprising the steps of:
   a. providing a synthetic peptide consisting essentially of the amino acid sequence Arg-Gly-Asp;
   b. coupling said peptide to an affinity matrix in an affinity column;
   c. running said cell extract preparation through the column so as to achieve binding between the cell surface receptors to be isolated and said peptide;
   d. eluting said column with a solution containing a substance which selectively elutes said cell surface receptor; and
   e. collecting said cell surface receptors eluted thereby.

2. The method of claim 1, wherein the affinity matrix is SEPHAROSE beaded agarose matrix.

3. The method of claim 1, wherein said substance comprises said synthetic peptide consisting essentially of the amino acid sequence Arg-Gly-Asp.

4. The method of claim 1, wherein said synthetic peptide consisting essentially of the amino acid sequence Arg-Gly-As is the peptide Gly-Arg-Gly-Asp-Ser-Pro.

5. The method of claim 1, wherein said coupling step further comprises activating the SEPHAROSE beaded agarose matrix with cyanogen bromide.

6. The method of claim 1, wherein said cell extract preparation is derived from mesenchymal cells.

7. The method of claim 1, wherein said cell extract preparation is derived from osteosarcoma cells.

8. The method of claim 1, wherein said cell extract preparation is derived from fibroblast cells.

9. The method of claim 1, wherein said cell extract preparation is derived from platelets.

* * * * *